US011383131B2

(12) United States Patent
Bridges et al.

(10) Patent No.: US 11,383,131 B2
(45) Date of Patent: Jul. 12, 2022

(54) FUNCTIONAL CAPACITY EVALUATION SYSTEMS AND METHODS

(71) Applicants: Tony Bridges, Wetumpka, AL (US); Steven F. Windham, Birmingham, AL (US)

(72) Inventors: Tony Bridges, Wetumpka, AL (US); Steven F. Windham, Birmingham, AL (US)

( * ) Notice: Subject to any disclaimer, the term of this patent is extended or adjusted under 35 U.S.C. 154(b) by 473 days.

(21) Appl. No.: 16/600,199

(22) Filed: Oct. 11, 2019

(65) Prior Publication Data

US 2020/0114205 A1 Apr. 16, 2020

Related U.S. Application Data

(60) Provisional application No. 62/804,762, filed on Feb. 13, 2019, provisional application No. 62/744,133, filed on Oct. 11, 2018.

(51) Int. Cl.
| | | |
|---|---|---|
| *A63B 24/00* | (2006.01) | |
| *A63B 21/00* | (2006.01) | |
| *A63B 21/06* | (2006.01) | |
| *A61B 5/11* | (2006.01) | |
| *A61B 5/22* | (2006.01) | |
| *A61B 5/00* | (2006.01) | |

(52) U.S. Cl.
CPC ........ *A63B 24/0062* (2013.01); *A61B 5/1124* (2013.01); *A61B 5/224* (2013.01); *A61B 5/6887* (2013.01); *A63B 21/0605* (2013.01); *A63B 21/4035* (2015.10); *A63B 21/4043* (2015.10); *A63B 24/0003* (2013.01); *A63B 24/0087* (2013.01); *A61B 5/1126* (2013.01); *A61B 2505/09* (2013.01); *A63B 2024/0065* (2013.01)

(58) Field of Classification Search
CPC ............ A63B 24/0062; A63B 21/4035; A63B 21/4043; A63B 21/0605; A63B 24/0003; A63B 24/0087; A63B 2024/0065; A61B 5/1124; A61B 5/224; A61B 5/6887; A61B 5/1126; A61B 2505/09
USPC ...................................................... 73/379.01
See application file for complete search history.

(56) References Cited

U.S. PATENT DOCUMENTS

| | | |
|---|---|---|
| 5,142,910 A | 9/1992 | Litchman |
| 5,260,870 A | 11/1993 | Tsuchiya et al. |
| 5,271,416 A | 12/1993 | Lepley |
| 5,275,045 A | 1/1994 | Johnston et al. |

(Continued)

FOREIGN PATENT DOCUMENTS

| | | |
|---|---|---|
| EP | 1928317 B1 | 3/2011 |
| EP | 2823761 A1 | 1/2015 |

(Continued)

*Primary Examiner* — Octavia Davis Hollington

(57) ABSTRACT

Systems and methods are provided for testing the ability of an individual to lift objects under various conditions. During standard lifting tests, the average acceleration and velocity of each lift, as well as the distribution of force between the hands and feet of the patient, are electronically measured and recorded. These objective factors can then be used to determine whether the patient is exerting maximal effort, and to assess a patient's condition and progress during a rehabilitation program. In example embodiments, one or more components of the system are adjustable so as to accommodate users of various posture, mechanics, size and movement capabilities.

16 Claims, 9 Drawing Sheets

(56) References Cited

U.S. PATENT DOCUMENTS

| | | | |
|---|---|---|---|
| 5,348,519 | A | 9/1994 | Prince et al. |
| 5,437,587 | A | 8/1995 | Prince et al. |
| 5,456,648 | A | 10/1995 | Edinburg et al. |
| 5,891,042 | A | 4/1999 | Sham et al. |
| 6,056,671 | A | 5/2000 | Marmer |
| 6,086,517 | A | 7/2000 | Schapmire |
| 6,216,535 | B1 | 4/2001 | Schapmire |
| 6,227,047 | B1 | 5/2001 | Livingston |
| 6,672,157 | B2 | 1/2004 | MacFarlane et al. |
| 6,904,801 | B1 | 6/2005 | Bridges et al. |
| 7,146,855 | B1 | 12/2006 | Chang et al. |
| 7,761,140 | B2 | 7/2010 | Kontothanassis et al. |
| 9,836,118 | B2 | 12/2017 | Steele |
| 10,045,895 | B2 | 8/2018 | Eklof et al. |
| 10,251,796 | B2 | 4/2019 | Eriksson et al. |
| 2008/0183050 | A1 | 7/2008 | Kontothanassis et al. |
| 2010/0268374 | A1* | 10/2010 | Jung ................. H01L 21/67265 414/280 |
| 2020/0222760 | A1* | 7/2020 | Padgett .............. A63B 24/0087 |

FOREIGN PATENT DOCUMENTS

| | | | |
|---|---|---|---|
| EP | 2823761 | A4 | 4/2015 |
| WO | 2007036611 | A1 | 4/2007 |
| WO | 2008094981 | A2 | 8/2008 |
| WO | 2008094981 | A3 | 10/2008 |
| WO | 2013028961 | A1 | 2/2013 |
| WO | 2013132129 | A1 | 9/2013 |

* cited by examiner

Testing Console

| 2018-11-21 | Floor | Waist | | Test Distance (in): 35.0 |
|---|---|---|---|---|

Time (sec): 0.00

Ave. Velocity (in/sec): 0.00
Ave. Accel. (in/sec2): 0.00
Force (ft.lbs): 0.00

Ave. Left Foot (lbs): 0.00
Ave. Right Foot (lbs): 0.00
Foot Disparity: 0.00

[Graph] — 240

| Weight (lbs) | Distance (in) | Time (s) | Average Velocity (in/s) | Average Accel (in/s^2) | Average Force (ft.lbs) | Average Left Foot (lbs) | Average Rgt. Foot (lbs) | Foot Disparity (%) |
|---|---|---|---|---|---|---|---|---|
| 15 | 35.0 | 0.90 | 38.9 | 43.3 | 649.6 | 94.6 | 111.0 | 14.8 |

}— 210

Weight: 20 lbs  [-] [+]  — 220

Start Test — 230

Main — 232

FUNCTIONAL CAPACITY EVALUATION SYSTEMS AND METHODS

CROSS-REFERENCE TO RELATED APPLICATION

This application claims priority to U.S. Provisional Patent Application Ser. No. 62/744,133 filed Oct. 11, 2018 and U.S. Provisional Patent Application Ser. No. 62/804,762 filed Feb. 13, 2019, the entireties of which are incorporated by reference herein in their entirety.

TECHNICAL FIELD

This invention is related to the field of human functional capacity testing. In particular, the invention provides systems and methods for testing the ability of an individual to lift objects under various conditions, and for objectively determining whether the individual is exerting maximal effort during such tests.

BACKGROUND OF THE INVENTION

In the field of physical medicine and rehabilitation, various professionals are often called upon to assess the functional capacity of a patient. Functional Capacity Evaluations ("FCEs") are used extensively throughout the United States to ascertain an individual's status in regards to the extent of a disability and/or the ability to return to work. FCEs have assumed particular importance in light of the high cost of worker's compensation claims for industrial accidents.

The ability to lift is one of the critical factors affecting a patient's ability to return to work. Thus one of the most important functions of an FCE is determining the patient's ability to lift particular amounts of weight in particular configurations, including floor to shoulder, floor to waist, knuckle to shoulder, and shoulder to overhead. The question with such tests, however, is always whether the patient has given maximal effort, so that the results of the test present a true picture of the patient's functional capabilities.

At present, there is no system which can accurately determine whether a patient has given maximal effort. While indicators such as mechanical breakdown, postural breakdown, recruitment of accessory muscles, and heart rate may be used, the application of these indicators is to some degree subjective and thus subject to question. Furthermore, many evaluators administering FCE's may have inadequate experience to determine whether true maximal effort was given.

While patients have been known to manipulate FCE results by conscious and unconscious efforts, there are certain variables that cannot be manipulated. In particular, as maximal effort and maximal weights are achieved, the expected outcome is slower time to complete the lift, along with decreased velocity and acceleration.

The most widely given reason for inability to lift additional weight is pain. Pain has been shown to result in decreased range and velocity of motion for affected body segments. It is also well known that when pain is present it affects the strength of muscular contraction. Therefore, if pain is truly present in a given lift, the variables of speed, velocity, and acceleration will be adversely affected. Test results which are inconsistent with these expectations (for example where velocity and acceleration does not decrease significantly between a previous lift and a lift with greater weight claimed to represent "maximal effort," or where the velocity and acceleration for two lifts of the same weight during different portions of an FCE vary dramatically) may indicate that the patient is not expending maximal effort, or is otherwise attempting to manipulate the test results.

The force distribution between the patient's legs when performing lifts is another objective factor which can be taken into account in assessing functional capacity, particularly for patients who claim either lower back or lower extremity pathology. Many patients with spinal disc pathology have symptoms related to one of the lower extremities, which may impair strength and sensation as well as functional status (e.g. the ability to squat, kneel, climb stairs, lift, etc.). Patients manipulating the system may consciously walk with an antalgic gait and shift their weight more to one side when standing, but during a lift will often unconsciously apply force symmetrically on both legs, thereby illustrating their actual functional status with respect to the allegedly "weak" leg. Measuring force distribution during lifting may also give a physician or rehabilitation professional valuable information regarding the patient's diagnosis and progress during a rehabilitation program.

Likewise, the force distribution between the patient's hands during a lift may shed light on the true condition of patients complaining of pain or weakness in one arm due to upper back pathology or other causes. Further information regarding the relative strength of each arm may also be gathered by utilizing a program of one-armed lifts and collecting information on the velocity, acceleration, and force generated.

Several devices have previously been developed to measure these and other objective indicators during FCEs. For example, Marmer's "Functional capacity assessment system and method", U.S. Pat. No. 6,056,671, uses digitized video to determine the velocity and acceleration of lifts during a functional capacity evaluation. However, this system makes use of multiple video cameras and a computer system, as well as visual indicators which have to be applied to the patient. Accordingly, the system may be complex and expensive, and require substantial time to set up and operate, rendering it unsatisfactory for some FCE applications. Additionally, it provides no mechanism for measuring force distributions between the patient's hands and feet.

Lepley's "Exercise platform for physiological testing," U.S. Pat. No. 5,271,416, also can be used to collect lift velocity and acceleration information, as well as data regarding the force applied by the patient's feet (though not hands) during a lift. However, this system uses a cable spool with a handle to simulate the lifting of an object, and so may not accurately reproduce the circumstances encountered in a "real world" lift, which is a primary goal in the development of FCE test protocols.

U.S. Pat. No. 6,904,801 to Bridges et al. discloses a functional capacity evaluation apparatus for collecting velocity, acceleration, and force distribution data regarding the lift data of a patient. However, many problems exist with respect to the device's functionality, measuring capabilities, adjustability, ease of use, data collection, etc. For example, depending on the patient's posture, mechanics, size and movement capabilities, the apparatus thereof may not function as desired, for example, as the sensors could interfere with one or more portions of the patient's body, and thus, unintentionally trigger the system and provide faulty data. Furthermore, other aspects of the apparatus do not provide for adjustment thereto, and thus, have been known to not accommodate every user desiring to be evaluated.

Moreover, the data obtained from the user's lifting must be manually compiled/collected, and for example, must be manually exchanged with one or more other parties of interest (e.g., insurance company, employer, etc.). And other important data associated therewith must also be manually collected and distributed, for example, which has known to be incorrect and unreliable. For example, since the user or other assistant manually collects/inputs at least some of the data regarding the user's lift(s), there is a higher risk of inaccurate data which can be in part due to human error.

Accordingly, it would be advantageous to have a system for use in FCE testing which could accurately collect and disribute velocity, acceleration, and force distribution data in a test format which is already familiar to FCE evaluators and closely mimics actual dynamic lifting conditions, which is adaptable with patient's of various postures and mechanics, while being relatively inexpensive to manufacture, and easy to set up and operate.

It is to the provision of the functional capacity evaluation systems and methods described herein that the present invention is primarily directed.

SUMMARY OF THE INVENTION

In example embodiments, the present invention provides functional capacity evaluation systems and methods.

It is the primary object of the present invention to provide systems and methods for testing the ability of an individual to lift objects under various conditions, and for objectively determining whether the patient is exerting maximal effort during the tests. In the systems and methods as disclosed herein, standard lifting tests are conducted in a manner well known in the art. The average acceleration and velocity of each lift, as well as the distribution of force between the hands and feet of the patient, is electronically measured and recorded. These objective factors can then be used to determine whether the patient is exerting maximal effort.

According to some example embodiments of the present invention, one or more of the sensors of the functional capacity evaluation systems and methods are movable so as to adjust the position of the sensor relative to a front shelf of the system, or to adjust to other portions of the device so as to be adjustable based on the particular subject. According to some example embodiments, one or more of the sensors can be pivotable between an inwardly-spaced position and an outwardly-spaced position, for example, to provide at least some adjustability to the spacing of the one or more sensors relative to the front shelf of the system.

In one aspect, the present invention relates to a functional capacity evaluation system including a rack, a standing platform, at least one shelf, and at least one sensor attached to the rack nearby the shelf. In example embodiments, the sensor is adjustable between an extended position and a retracted position, and wherein the at least one sensor is repositionable between a substantially horizontal orientation and a substantially vertical orientation in either of the extended or retracted configurations.

In example embodiments, the system further includes at least one arm portion movably mounted to the rack, and wherein the at least one sensor is mounted to at least a portion of the arm portion. In example embodiments, the system further includes at least one force sensor provided with the standing platform so as to measure one or more separate loads applied thereto. In example embodiments, the arm portion generally extends outwardly from the rack or shelf nearby, and wherein the arm portion comprises a fastener so as to provide adjustability to the same between the substantially horizontal orientation and the substantially vertical orientation.

In example embodiments, the at least one arm portion is movably mounted to the rack and configured to both traverse between the expanded and retracted configurations and pivot between a substantially horizontal orientation and a substantially vertical orientation. In some example embodiments, at least two arm portions are movably mounted on opposite sides of the at least one shelf, wherein the arm portions are adjustable between an expanded and retracted configurations. In example embodiments, the arm portions are further adjustable between a substantially horizontal orientation and a substantially vertical orientation.

In example embodiments, the system further includes a control system connected to the at least one sensor and an electronic device, wherein data output from the at least one sensor is received by the control system, and wherein the control system outputs the data to the electronic device. In example embodiments, the electronic device receives the data from the control system and outputs the same to a visual screen thereof, the data corresponding to at least one parameter selected from the group consisting of the weight of a lifting box, the distance of the lift, the time or duration of the lift, average velocity, average acceleration, average force, the average loads of each foot of the user during the lift, or the foot disparity between the average loads of each foot.

In another aspect, the present invention relates to a functional capacity evaluation system including a rack, a standing platform, at least one sensor, a control module and an electronic device. The rack has at least one shelf and the standing platform is generally positioned on a ground surface near the rack. The at least one sensor is mounted to at least a portion of the rack. The control module is connected to the at least one sensor and the electronic device is connected with the control module. In example embodiments, the electronic device includes an application such that data from the at least one sensor can be collected, processed, calculated and displayed on the electronic device.

In example embodiments, the system further includes a server or database for collecting and storing data obtained from the at least one sensor, control module and/or electronic device, wherein the control module and/or electronic device are connected to a network, and wherein the database is connected to the network so as to provide a channel of communication between the server and the control module and/or electronic device such that data can be sent and received therebetween.

In example embodiments, the system further includes a lifting box, the lifting box including at least one grasping handle and a retaining area such that one or more weights or weighted objects can be contained therein. In example embodiments, the system further includes a second electronic device coupled with at least a portion of the lifting box, the second electronic device configured to communicate with the control module, the electronic device and/or the database. In example embodiments, the second electronic device is configured to obtain data in real time related to the movement, position, orientation, velocity and/or acceleration of the same and lifting box thereof when a user lifts the lifting box.

In example embodiments, the at least one sensor comprises a proximity sensor, the proximity sensor being in communication with the second electronic device such that the position of the second electronic device and lifting box thereof relative to the proximity sensor can be captured in real time. In example embodiments, the second electronic device can obtain its position in three-dimensional space relative to the proximity sensor. In example embodiments, the system further includes at least one load cell or sensor mounted to the standing platform.

In yet another example embodiment, the present invention relates to a method of using a functional capacity evaluation system including providing a functional capacity evaluation rack including a standing area or platform, one or more height-adjustable shelves, and at least one arm support member, the arm support member including a sensor mounted thereto; providing a lifting box to be lifted by a user; providing at least some adjustment to the at least one arm support member and sensor mounted thereto, the at least one arm support member being adjustable between a generally horizontal orientation and a generally vertical orientation; and performing at least one lift, wherein a user lifts the lifting box from the standing area to a desired height, wherein the at least one sensor captures the user's lift movement so as to provide data related to the time at which the user both begins and completes the lift.

In example embodiments, the method further includes providing a control module for collecting the data from the at least one sensor. In example embodiments, the method further includes providing an electronic device for collecting the data from the at least one sensor.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of the invention are exemplary and explanatory of preferred embodiments of the invention, and are not restrictive of the invention, as claimed.

BRIEF DESCRIPTION OF THE DRAWINGS

FIG. 12 shows a screen capture of an electronic device that is configured to be linked with the functional capacity evaluation system according to another example embodiment of the present invention.

DETAILED DESCRIPTION OF EXAMPLE EMBODIMENTS

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Figure 1:
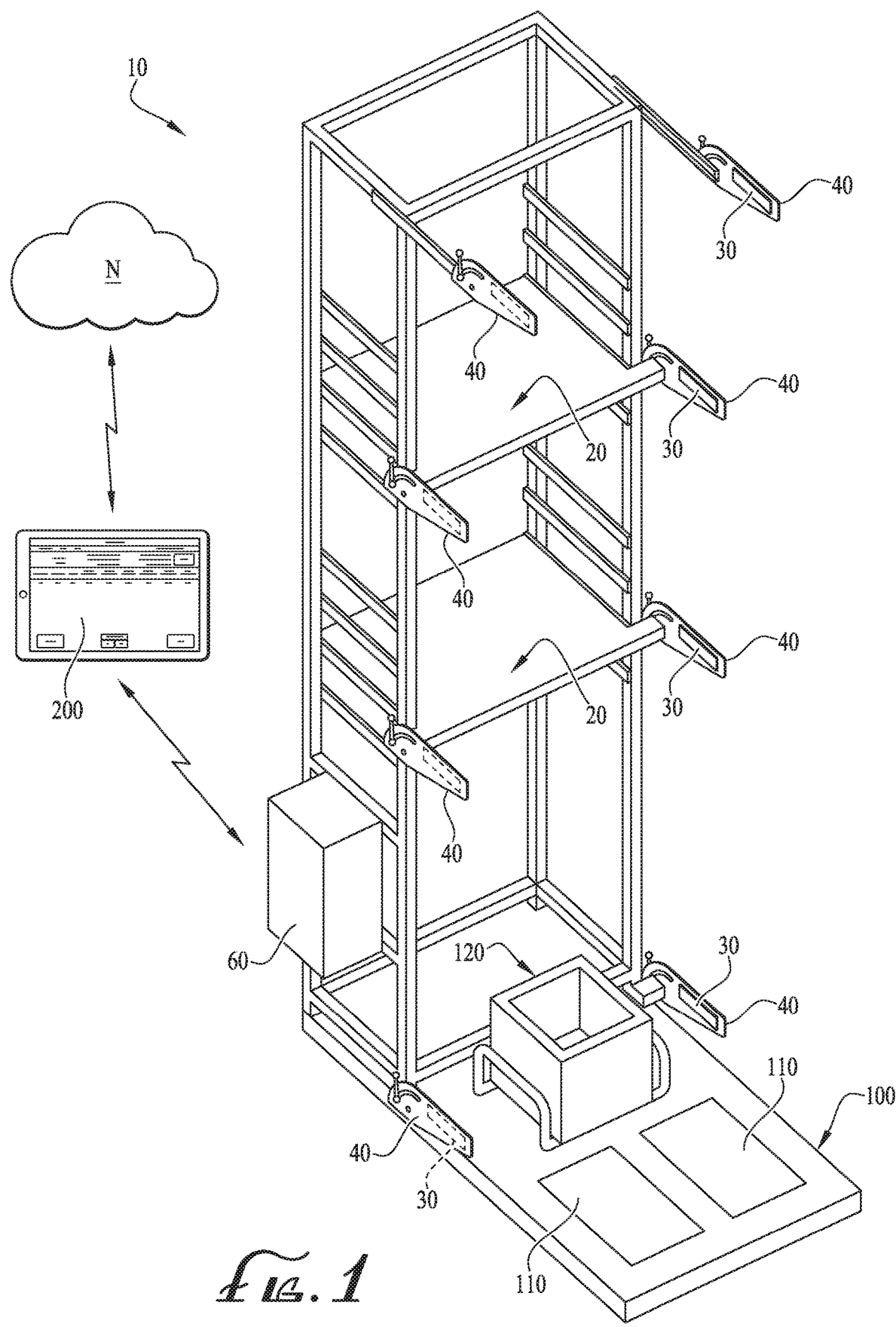
FIG. 1 shows a functional capacity evaluation system according to an example embodiment of the present invention.

With reference to the drawings, FIG. 1 shows functional capacity evaluation system 10 according to an example embodiment of the present invention. In example embodiments, the system 10 comprises a rack 12, of a type in common use in the FCE industry, for providing support for one or more surfaces or shelves 20. One or more support arms 40 (and sensors 30 mounted thereto) are movably mounted to the shelves 20 and/or one or more portions of the system 10, for example, to provide for adjustability to how the one or more sensors 30 collect data relative to a user's posture, mechanics, size and flexibility.

In example embodiments, a lifting box 120 is provided and generally comprises one or more grasping portions and an open area for temporarily holding/containing one or more weights or weighted objects. In one example embodiment, the grasping portions extend along the outer sides of the box 120, for example, generally extending between the front and back sides of the box 120 along the sides between the front and back sides. In other example embodiments, the handles extend outwardly from opposite sides of the box 120 (see handle 353 of FIG. 14). In example embodiments, the handles extend generally perpendicular relative to the surface or member it's extending from (e.g., two generally opposite sides). In other example embodiments, the handle(s) can be configured as desired. In example embodiments, a user U or patient grasps the one or more handles and lifts the box 120 (with and without weights) to one or more heights/shelves 20 such that the data obtain by the sensors can be obtained to indicate maximal lift capacity of a user or patient.

In example embodiments, a control module 60 is mounted to a portion of the rack 12 and comprises the necessary hardware and software, processors, microcontrollers and/or other components so as to collect the data obtained from the sensors 30. In example embodiments, the control module 12 comprises a power supply and is powered by electricity, for example, standard 120V. In example embodiments, each sensor 30 is wired directly to the control module 60. According to example embodiments, the sensors 30 are in the form of a laser or of the break/interference or photogate-type. In some example embodiments, proximity sensors, RFID tags or readers, other IR or RF devices or other communication devices can be provided so as to understand when a portion of the user (or the box 120) reaches a certain position and/or height, location, etc. In other example embodiments, the sensors can be chosen as desired, for example, of either of the analog or digital type.

As depicted in FIG. 1, the control module 60 can communicate directly with an electronic device 200 (also see FIGS. 12-14), for example, such that any data (e.g., data obtained from the sensors 30 and any other data input) can be used to perform one or more calculations, provide graphs of one or more lifts, and ultimately, provide a beneficial, adjustable, and error-free system to indicate maximal lift capacity of a user or subject. According to some example embodiments, the control module 60 and the electronic device 200 are wirelessly connected by use of a Bluetooth connection. In other example embodiments, the control module 60 can comprise its own network, for example, such that the electronic device connects to the Wi-Fi network of the control module 60, for example, such that data can be transmitted therebetween. In some example embodiments, the control module can be directly connected to the internet via a CAT-5 cable, for example, wherein the cable is connected to the network of the office or building space where the system 10 is located. In other example embodiments, the control module 60 and electronic device 200 can be connected together as desired so as to be able to transfer data therebetween.

In example embodiments, the electronic device 200 preferably comprises an application and/or other hardware and software such that data obtained by the control module 60 can be further distributed to the electronic device 200. In example embodiments, the application can comprise various capabilities (see FIGS. 12-14), for example, which is beneficial in demonstrating a consistent decrease in acceleration with increasing loads due to the diminishing ability to generate force. In example embodiments, the application can comprise requirements such as a username and password, for example, such that trainers or therapist (or doctors) have their own unique name and password, and thus, can gain access to the system and connect with the control module 60. The control module 60 and/or electronic device 200 can be connected to Wi-Fi or can comprise components for obtaining a cellular connection such that one or the other is connected to the internet N. In example embodiments, a cloud server or other database/data collection network is provided and connected to the internet N, and for example connectable with the control module 60 and/or the electronic device 200.

Preferably, the control module and/or electronic device 200 communicates with the server via Wi-Fi or cellular such that the data collected, obtained and processed for each user is further collected on the server. In example embodiments, the server collection process is especially desirable when multiple machines are used in multiple locations, which process and test multiple users or patients. In some example embodiments, the therapist can log in to their profile on the internet, and for example, have access to each user that is associated with their username, or for example, each username can be connected with other usernames such that each therapist in an office, location, region or company worldwide can access any of the patients test data. As described above, all data obtained during one or more tests as described herein can be collected on the server in addition to being processed by the electronic device 200.

In example embodiments, the rack 12 allows for repositioning of the one or more shelves 20, for example, wherein the one or more shelves 20 can be positioned up to about 76 inches or more from the ground, for example, so that a user or patient can lift the box 120 (with or without weights therein) from the ground surface to one or more of the shelves 20, or for example, for placement atop an upper surface of the desired or target shelf 20.

In example embodiments, at least one support or arm 40 (and sensor 30 attached thereto) is provided on at least one side of each shelf 20 or level where data is desired to be collected. For example, as shown in FIG. 1, at least one support arm 40 (and sensor 30 attached thereto) is provided near a support platform or base 100 (e.g., for triggering an initial "start lift" time-stamp when the user lifts the box 120), and at least one support arm 40 having the sensor 30 mounted thereto is mounted to at least one side of the shelves positioned at heights associated with a patient's waist and shoulders. Furthermore, at least one support arm 40 can be translatably mounted to at least one side of an upper portion of the rack 12, for example, so as to provide a sensor 30 (e.g., data collector) that is positioned for an upper reach or top shelf-type lift.

In some example embodiments as depicted in FIG. 1, an elongate and generally rigid member is translatably mounted to each outer and upper side of the rack 12, for example, so as to be moveable between a collapsed or retracted position and an extended or expanded position. In example embodiments, the support arms 40 (and sensors 30 mounted thereto) are preferably adjustable so as to be positioned for accurate data based on the user, for example, such that the user can place their feet in defined rectangular areas (e.g., load cells 110) of the base 100 and lift the lifting box 120 (resting atop the base 100) to cause interference with the sensors 30 of the support arms 40 that are moveably mounted about 70-100 inches above the ground surface or base 100. In example embodiments, a fastener, knob and bolt locking pin, clamp or other temporary securing device can be provided for removably securing the movably-mounted elongate members to the rack 12.

In example embodiments and as described above, the support arms 40 (and sensors 30 attached thereto) are provided near each of the one or more shelves 20 so as to capture/trigger a time stamp as to when the box 120 is lifted (e.g., interference between sensors 30 when the box 120 is resting and immediate contact of the sensors 30 when the box 120 is lifted), and when the box 120 lifted to a desired height or position (e.g., sensors 30 at heights of the one or more shelves 20 or upper lift height remain connected and communicating with each other until the user or the box 120 thereof causes interference).

For example, according to one example embodiment, a support arm 40 and a sensor 30 (mounted to the support arm 40) is provided on each side of each shelf 20, and for example, on either side of a standing platform 100. According to one example embodiment, the sensors 30 are generally co-planar and aligned such that any object passing therebetween triggers the sensors (e.g., causes interference between the sensors 30) and a time stamp is collected by the. According to another example embodiment, each shelf only comprises a single sensor 30, or for example any other sensor, motion capture or other device(s) or system(s) so as to determine when the user begins the lift and when the user passes a particular height during a lift and/or sets the box 120 atop one or more of the shelves 20.

The support arms 40 are generally pivotally mounted to the shelf 20, a portion of the rack 12 or other portions or components as desired, for example, so as to provide for the ability to pivot between a substantially horizontal orientation and a substantially vertical orientation. In one example embodiment, a fastener is received within an arcuate or curved channel of the support arm and a separate bolt or pivot acts as the axis about which the support arm can pivot. Loosening of the fastener allows the support arm to pivot about the bolt. The ends of the arcuate channel define the bounds (e.g., min and max) of which the support arm can pivot. In one example embodiment, the curved channel is configured to permit the support arm to move about 90 degrees. In other example embodiments, the channel can be configured so as to permit 360 degrees of rotation as desired.

Figure 2:
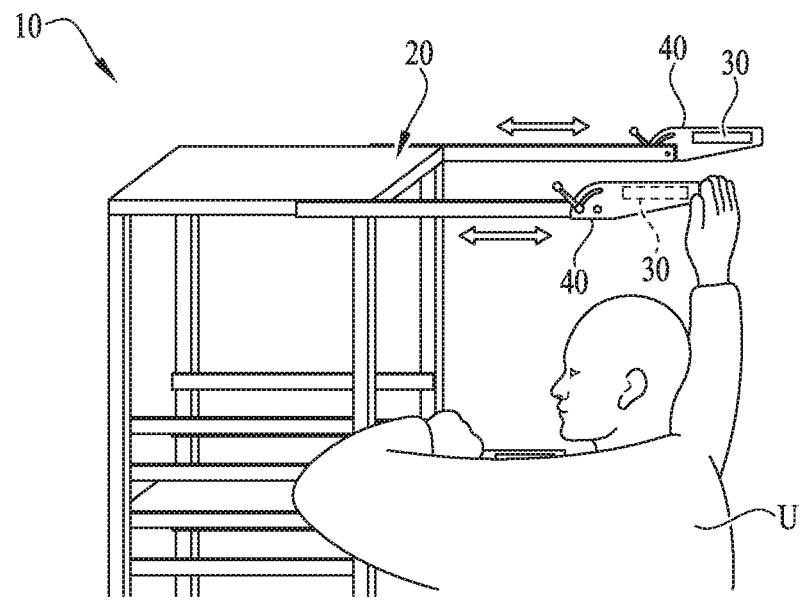
FIG. 2 shows a user providing adjustment to at least one arm and sensor component of the system of FIG. 1, the arm and sensor component thereof being in an expanded configuration.
Figure 3:
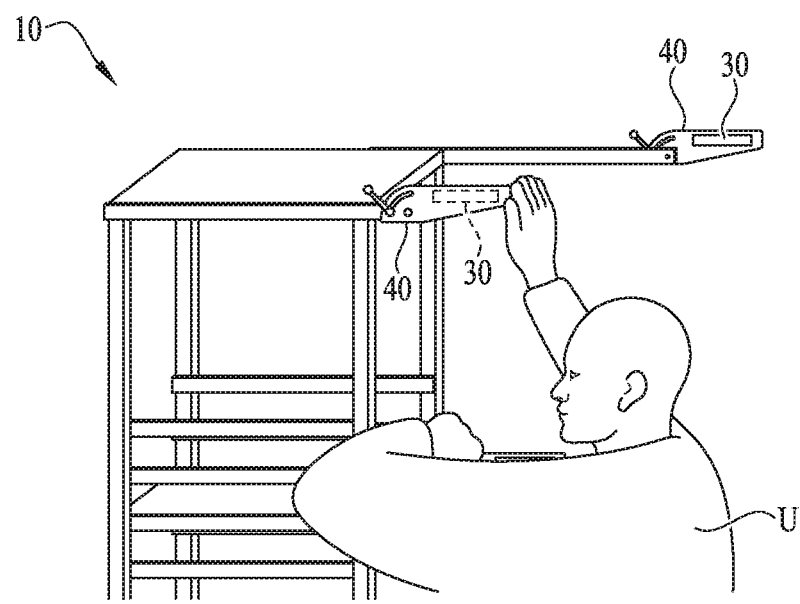
FIG. 3 shows the user of FIG. 2 placing the at least one arm and sensor thereof in a retracted position.

According to example embodiments of the present invention, one or more of the sensors 30 of the functional capacity evaluation system 10 are movable/adjustable so as to adjust the position of the sensor relative to a front shelf of the system, or to adjust to other portions of the system so as to be adjustable based on the particular subject or user being evaluated. For example, depending on the subject's posture, mechanics, size and flexibility, the sensors can be adjusted so as to provide functionality to the sensors and other measuring devices without being in a position that would cause unintentional triggering thereof due to the subject's posture. According to some example embodiments, one or more of the sensors 30 (and supports 40 thereof) can be traversable between a retracted position and an extended position (see FIGS. 1-3). According to some example embodiments, in addition to being traversable or extendable, the supports 40 are further pivotable between a horizontal orientation and a vertical orientation.

Figure 7:
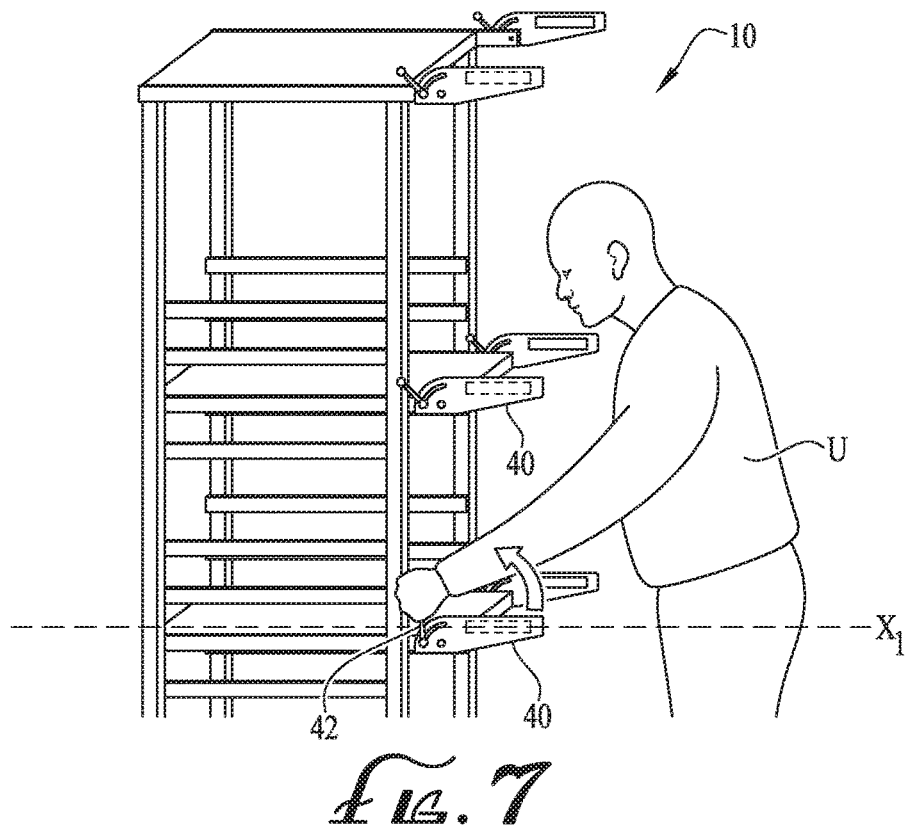
FIG. 7 shows the user providing adjustment to at least a portion of the arm or sensor portion of FIG. 6, wherein the user loosens a fastener that is retaining the arm portion and sensor thereof in the horizontal orientation so as to provide adjustment thereto.
Figure 8:
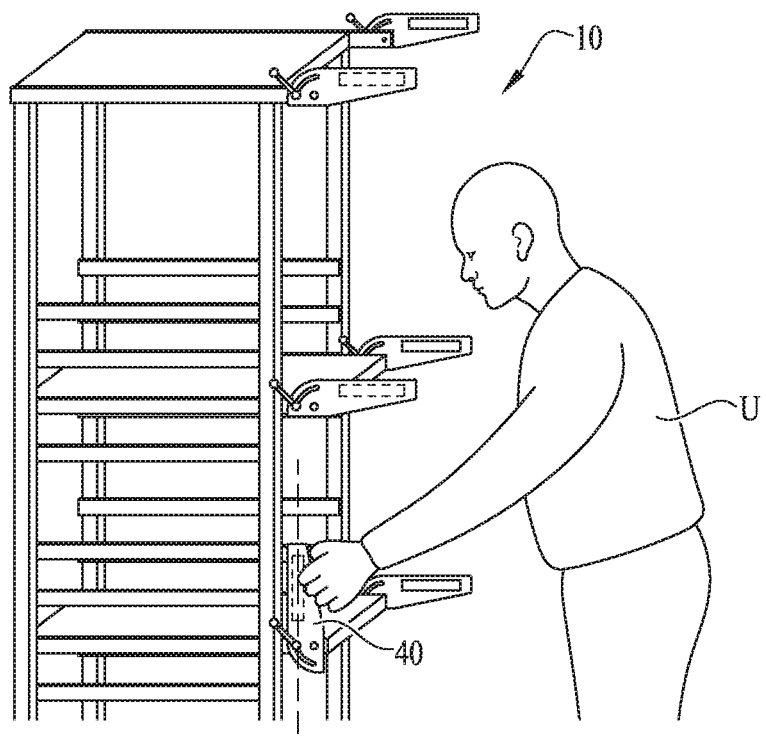
FIG. 8 shows the user of FIG. 7 positioning the arm portion and sensor thereof in a generally vertical orientation.

For example, according to some example embodiments, the one or more sensors 30 (and arms 40 thereof) are pivotable between a substantially horizontal orientation (FIGS. 4-7) and a substantially vertical orientation (FIGS. 8-11). According to another example embodiment, the sensors can be removably oriented at any angle defined between the substantially horizontal orientation and the substantially vertical orientation (e.g., 90 degrees). For example, according to one example embodiment, the arms 40 and sensors 30 thereof define an axis $X_1$ in the horizontal orientation and an axis $X_2$ in the vertical orientation (see FIGS. 7-8). According to one example embodiment, the axis $X_2$ is offset about 90 degrees relative to the axis $X_1$ in the counter-clockwise direction.

Figure 4:
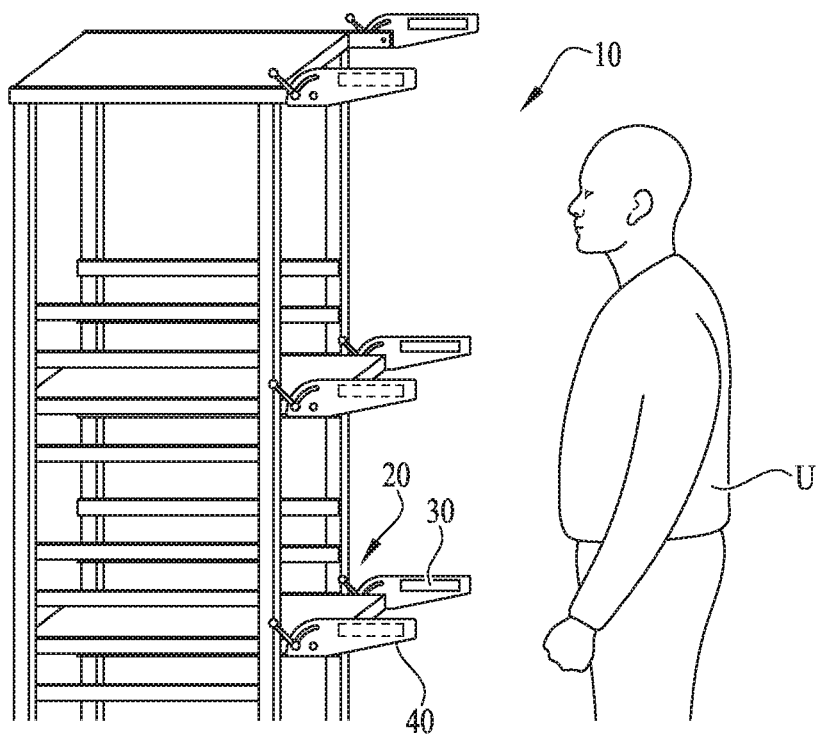
FIG. 4 shows a user standing upright near the system of FIG. 1 and prior to the attempt and completing a lift.
Figure 5:
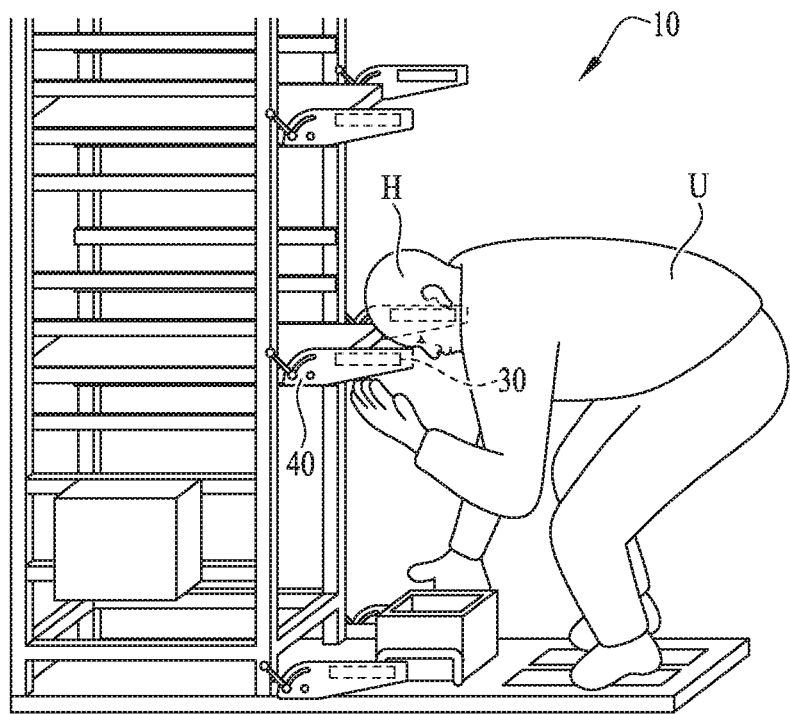
FIG. 5 shows a user squatting down to grasp a lifting box that is sitting atop a ground surface in front of the system of FIG. 1, and wherein squatting of the user in front of the system causes their head to unintentionally trigger at least one of the sensors prematurely.
Figure 6:
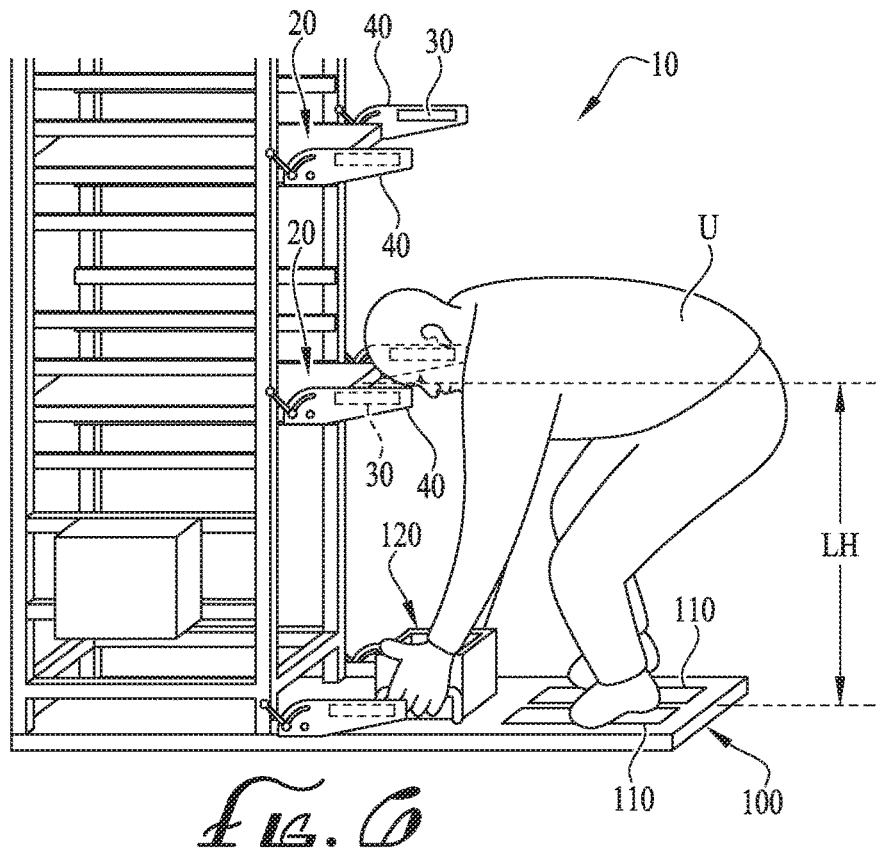
FIG. 6 shows the user of FIG. 5 grasping the lifting box and showing their head interfering with at least one of the sensors.
Figure 9:
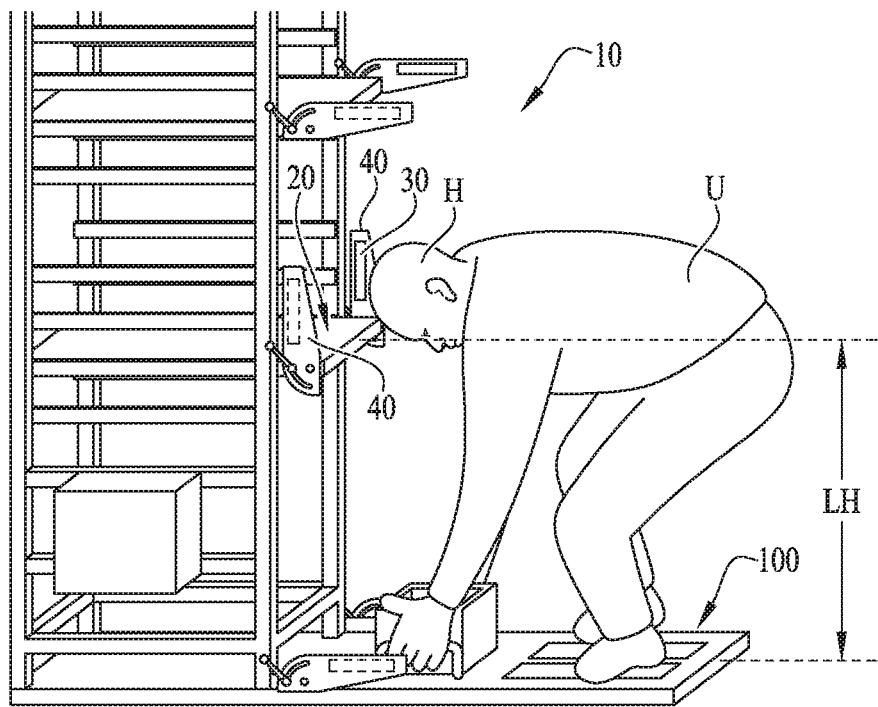
FIGS. 9-11 show the user of FIG. 5 completing a lift by lifting the lifting box from the ground surface to an elevated position, and wherein one or more arm portions and sensors thereof are oriented vertically so as to not unintentionally interfere with the user during a lift.
Figure 10:
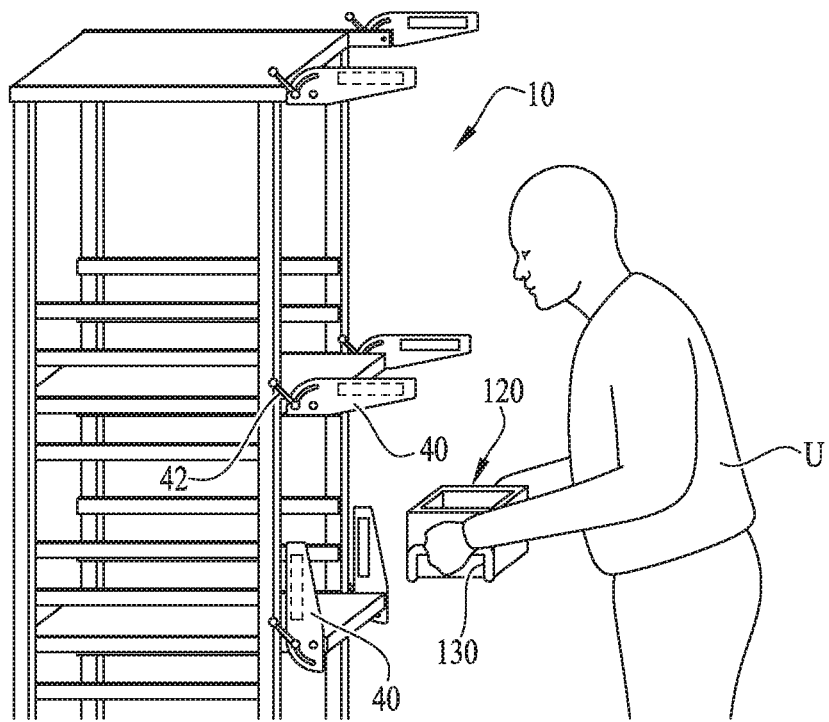
Figure 11:
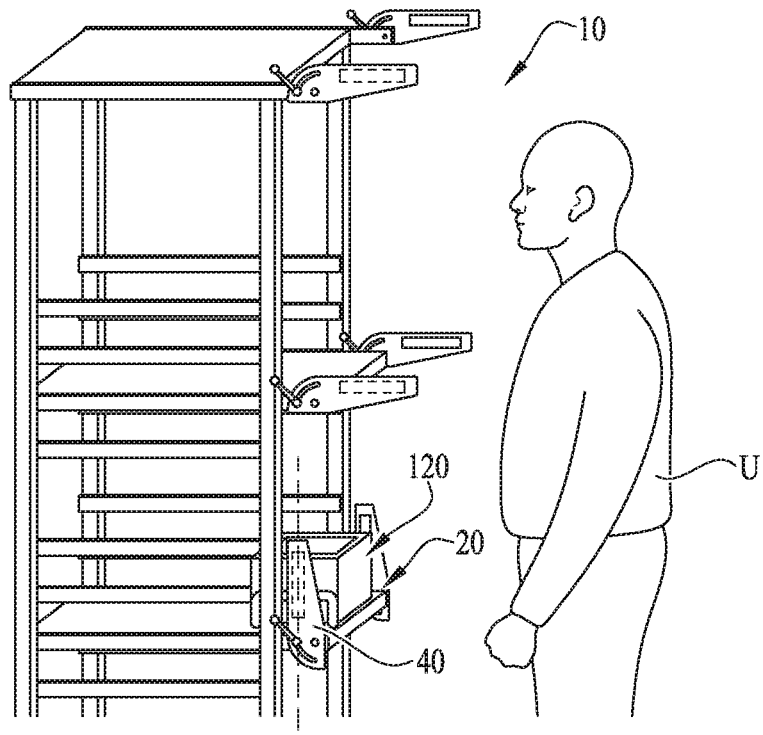

As depicted in FIGS. 4-5, when a patient's or user's U body interferes with the sensors 30 (e.g., a floor to waist movement where the head H interferes with the waist sensors 30 according to some example embodiments), one or more of the sensors 30 and/or arms 40 can be repositioned so as to not interfere with the user U during the lift or movement (e.g., picking the box 120 up by the handles 130 and raising it and setting it on the shelf 20—see FIGS. 9-11). Thus, while being in an orientation so as to not unintentionally trigger the sensors 30, the sensors 30 are still effective in capturing the time stamp of when the patient began entering the shelf at waist level (see FIGS. 10-11).

According to some example embodiments, one or more of the arms 40 and/or sensors 30 can preferably be movably mounted so as to automatically move to a desired position and/or orientation before, during and/or after the patient performs a lift, for example, to provide accurate data corresponding to the patient's lift and the load applied to the foot plates 110 (e.g., load cells) of the platform 100.

For example, according to one example embodiment, as the patient moves or lifts the box 120 from the platform 100 or one of the shelves 20 to another of the one or more of the shelves 20, one or more of the arms 40 and/or sensors 30 can be configured to automatically move to a desired position/orientation. Thus, according to example embodiments of the present invention, rather than the one or more arms 40 and/or sensors 30 being repositioned or reoriented manually, one or more of the arms 30 and/or sensors 40 can be automated and powered so as to provide movement/repositioning thereto without requiring manual repositioning thereof. According to example embodiments, the one or more arms 40 and/or sensors 30 can be linked with one or more motors, drivers, actuators, or other driving, rotary and/or movement devices so as to provide movement thereto. According to some example embodiments, one or more magnets and/or ferrous magnetic materials can be configured to provide a series or unique configuration so as to utilize electromagnetics to move and orient the sensors as desired, and for example, throughout the lift so that the time span from the patient lifting the box to the time the patient reaches the lift height LH of the lift is captured (see FIGS. 4-9). For example, according to example embodiments, rather than manually orienting the arms 40 and sensors 30 thereof so as to not interfere with the user's U body (e.g., and unintentionally trigger one or more of the sensors 30), the mechanics, posture, size of the patient can be assessed and visualized prior to performing any lifts (e.g., and data collection thereof). And after an assessment of the data, the one or more arms 40 and/or sensors 30 thereof can be programmed to reposition (once or multiple times) during the lift so as to not interfere with the patient's mechanics (e.g., and not unintentionally trigger the sensors 30) but to capture an accurate time stamp.

Figure 13:
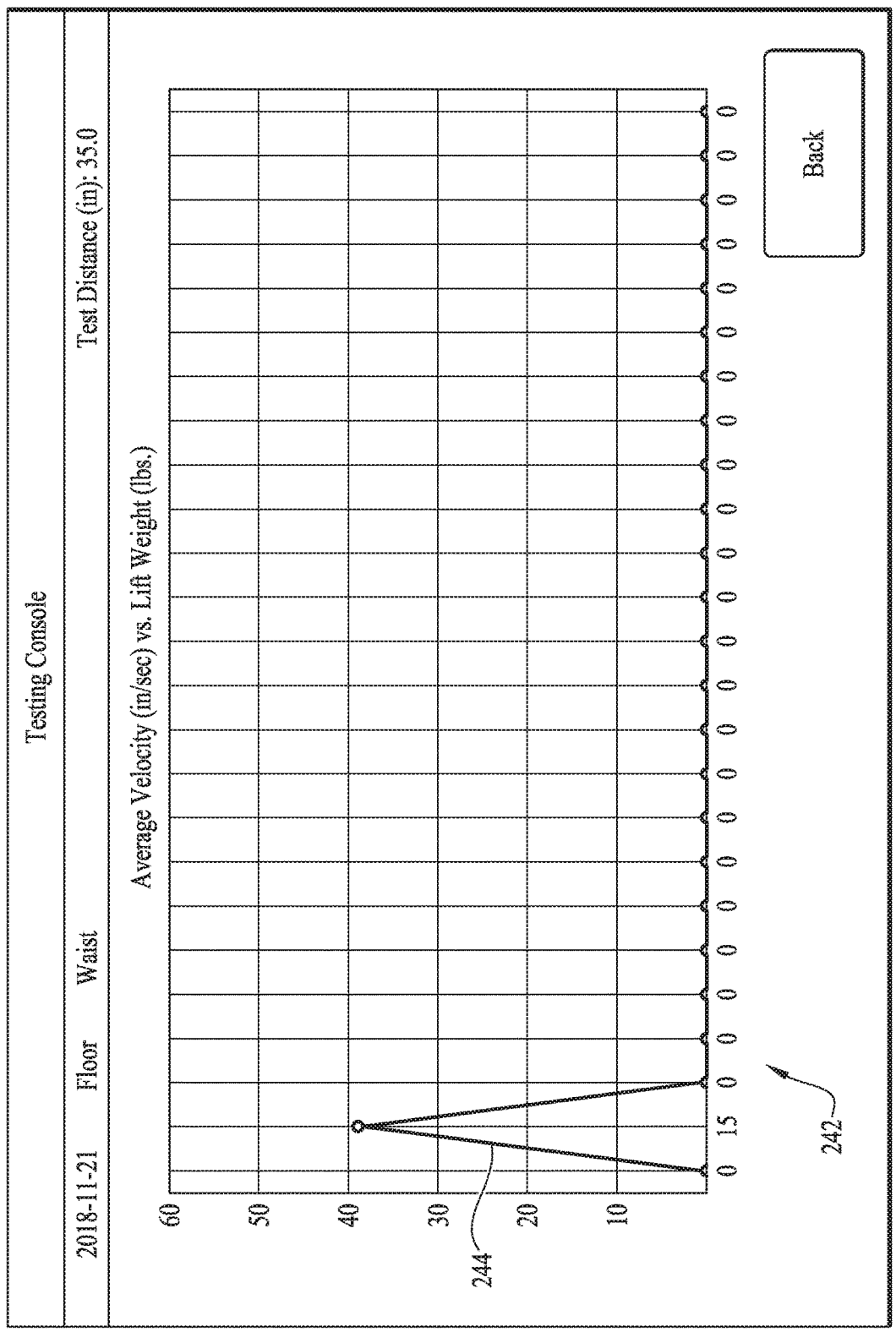
FIG. 13 shows a screen capture of an electronic device that is configured to be linked with the functional capacity evaluation system according to an example embodiment of the present invention.

FIGS. 12-13 shows a screen capture of an electronic device 200 according to an example embodiment of the present invention. In example embodiments, the electronic device 200 is preferably configured to communicate with the system 10 (and sensors 30, 110 thereof) such that the data captured during the one or more tests and/or lifts is collected and displayed on a screen of the electronic device 200. As depicted in FIG. 12, the data collected and displayed on the screen includes lift data 210 including the weight of the box 120 (optionally including the weight of one or more weights contained therein), the distance of the lift (e.g., distance between initial and ending position of the box lift), the time measured (s) from when the lift started to when the lift ended, average velocity (in/s), average acceleration (in/s$^2$), average force (ft. lbs), the average load applied to the plate 110 by the left foot—average left foot (lbs), the average load applied to the plate 110 by the right foot—average right foot (lbs), and the foot disparity (%) between the average left foot and average right foot. In example embodiments, additional features provided by the electronic device 200 include a toggle 220 for inputting the weight of the box 120, a "start test" button 230 to be pressed when the patient is to begin the lift, a main menu button 232, and a graph button 240, for example, to display a graph of data of a prior-performed lift. For example, as depicted in FIG. 13, a graph is provided on the screen of the electronic device 200 displaying the average velocity of the lift (e.g., 38.9 in/s) compared to the lift weight (e.g., 15 lbs) of the box 120 (and any additional weight added to the box 120). Optionally, other variables can be configured to be displayed on the graph.

According to example embodiments, the sensors 30 of the present invention are generally of the type that utilize infrared, laser, photoelectric or other technologies so as to allow for capturing one or more portions of the patient's body and/or box 120, for example, such that a time stamp is captured and collected, for example, such that the lift data can be captured and displayed on the electronic device 200. For example, according to some example embodiments of the present invention, the sensors 30 can comprise one or more individual beams passing from one of the sensors 30 to the corresponding and opposite sensor 30, for example, such that an object interfering with a line of sight between the corresponding sensors 30 causes a disruption therebetween, and thus triggers the sensors 30. According to another example embodiment, the sensors 30 project a generally solid band or curtain, for example, rather than individual beams. In other example embodiments, the sensors 30 can preferably be of other types and can be configured as desired. For example, according to some example embodiments, one or more sensors can be in the form of proximity sensors, or for example, other sensor technologies such that an object need not interfere with a line of sight provided between two sensors to cause the triggering thereof.

Figure 14:
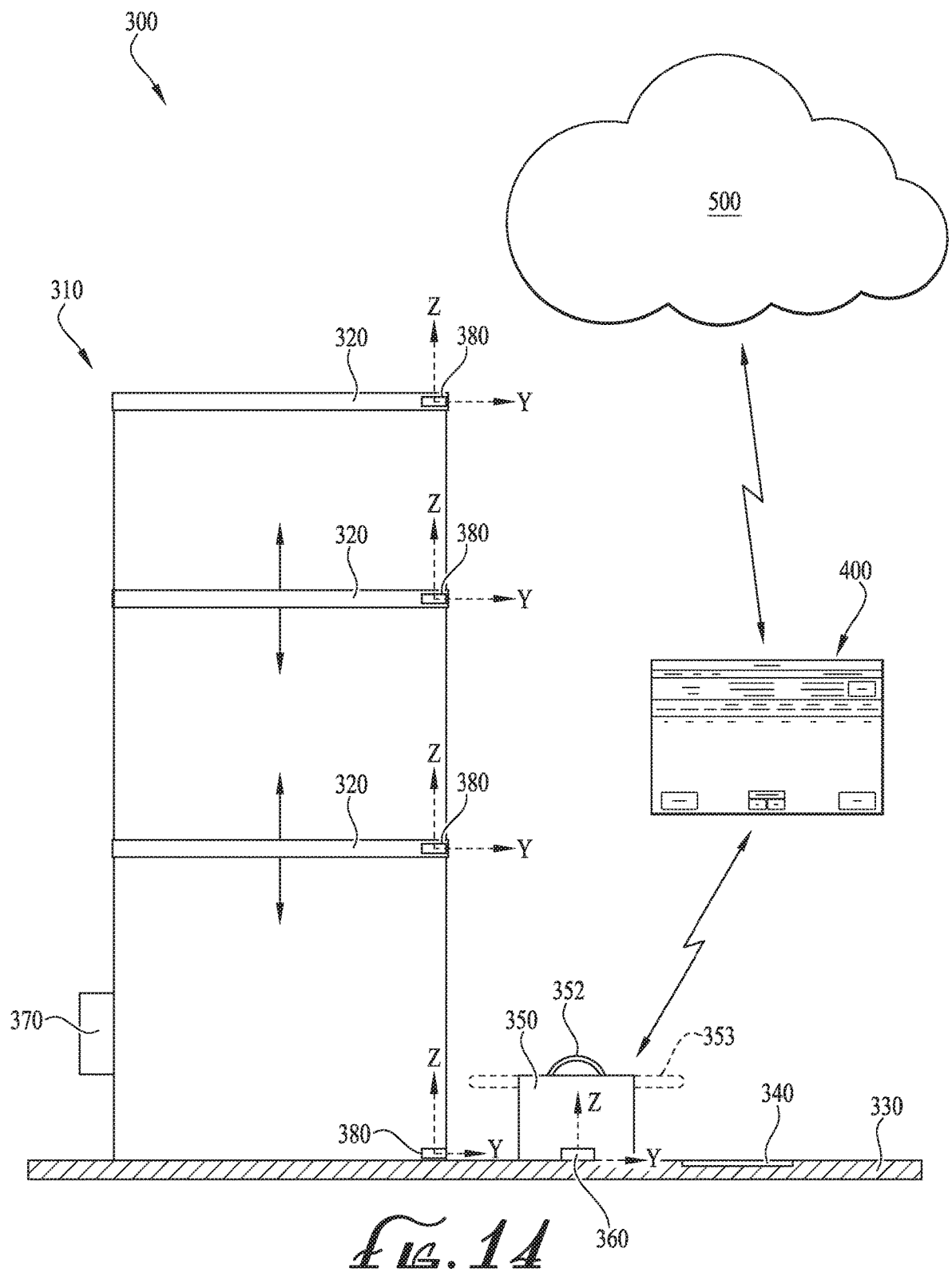
FIG. 14 shows a functional capacity evaluation system according to another example embodiment of the present invention.

FIG. 14 shows a system 300 according to another example embodiment of the present invention. In example embodiments, the system 300 comprises a rack 310 comprising one or more shelves 320, a standing platform 330 comprising foot plates 340 (e.g., force sensors), a lifting box 350, a control module 370 and at least one sensor 380 positioned near each of the one or more shelves 320. According to example embodiments, the one or more shelves 320 are generally positioned at heights associated with a patient's waist, shoulders and an upper reach or top shelf that is generally around 70-100 inches above the ground surface or platform 330 thereof. According to some example embodiments, the upper surface of the platform 330 is raised above the ground surface and the foot plates 340 are configured to be embedded in the platform 330. According to other example embodiments, the foot plates 340 are configured for setting atop the ground surface and are generally thin such that a mat or other covering can be provided. Optionally, one or more indicators are provided on the upper surface of the mat or covering so as to show the patient where to stand. In other example embodiments, the foot plates 340 can be configured as desired.

According to example embodiments, an electronic device 360 is generally movably mounted to a portion of the box 350. As described above, one or more weights can optionally be contained within the box so as to vary the weight thereof. According to some example embodiments, each of the weights can be configured to provide an indicator or other presence or location signal such that the electronic device 360 automatically obtains data relating to the amount of weight added to the box (and the total weight of the added weight plus the box). Thus, according to example embodiments of the present invention, the data relating to the weight of the box is sent from the electronic device 360 to the tablet 400 (optionally passing through the control module 370). So rather than the user or therapist manually entering the lift weight for each routine, this data is captured automatically and provides for the reduction of error.

Furthermore, as depicted in FIG. 14, the electronic device 360 comprises an accelerometer and/or other hardware/software so as to obtain the device's position, orientation, location, etc. in real time (e.g., see z axis and y axis). Thus, according to example embodiments of the present invention, the hardware and software of the electronic device 360 provides for the capability to collect the data associated with the movement of the electronic device 360 (and box 350 thereof) throughout the patient's lift (e.g., the electronic device 360 communicating with the electronic device 400). Thus, according to example embodiments of the present invention, the box 350 is provided with an on-board measurement device so as to provide data associated with one or more lifts of a patient.

For example, according to some example embodiments, with the control module 370 mounted to a portion of the rack 310, the electronic device 360 of the box 350 remains in constant communication with the control module 370, and wherein any movement of the electronic device 360 is sent therefrom to the control module 360, which is then further sent to the electronic device 400. Preferably, any movement of the electronic device 360 relative to the control module 370 can be accurately obtainable. For example, according to example embodiments, data corresponding to the precise distance the box 350 (and electronic device 360 thereof) moved throughout the lift is collected by the control module 370 and further processed as desired. For example, the movement distance can be in the form of the distance traveled in each axis (X, Y and Z) in three-dimensional space. In some example embodiments, the control module is not needed, for example, such that the electronic device 360 can independently obtain data associated with the movement and travel distance of the electronic device 360, for example, which can be communicated with the electronic device 400 as desired.

According to some example embodiments, one or more tags, markers and/or other indicators or sensors 380 (with or without power) are mounted to the one or more shelves 320 and ground surface or platform 330 of the rack 310. In example embodiments, the control module 370 and/or microprocessor(s) comprising hardware and software can be linked with the sensors 380 and/or foot plates. Optionally, the foot plates 340 and the sensors 380 can communicate directly with the electronic device 360, and thus, not require the control module 370 to function and record data. Accordingly, the timing and movement of lifting the box 350 between the ground surface or lift platform 330 and/or one or more of the shelves 320 is collected by the electronic device 360, and the data collected thereon is further communicated with the electronic device 400. In example embodiments, any data sent and/or captured by the electronic device 400 can be further collected in the cloud 500 or other available online or cloud-based network comprising a database or other data collection, storage and processing capabilities. According to one example embodiment of the present invention, the sensors 380 are in direct communication with the electronic device 360, and thus, all positional data of the electronic device relative to the one or more sensors 380 is collected for processing and calculations.

In some example embodiments, the at least one sensor that is mounted to at least a portion of the rack comprises a 3D capture sensor. The 3D capture sensor is preferably in communication the electronic device 360 such that the position of the same and lifting box thereof relative to the position of the 3D capture sensor, in three-dimensional space, can be captured in real time. Preferably, at least one of the electronic devices can provide one or more charts or graphs outlining/displaying the path, velocity, acceleration, force, weight of box, etc. as desirable.

Furthermore, according to example embodiments of the present invention, in addition to the electronic device 360 providing data relative to its position, orientation and location in real time, the velocity and acceleration of the same during the lift(s) can also be obtained. Furthermore, rather than the sensors 380 assisting with collecting data relative to triggering time stamps of when the box was lifted to when the box reached a certain height or its placement on a shelf 320, the electronic device 360 (and hardware and software thereof) can provide data relative to the time stamps of when the lift began to when the lift was completed. For example, according to one example embodiment, the time stamp associated with the initial lift movement of the box 350 (and electronic device 360) is captured (e.g., accelerometer senses movement and indicates that movement has occurred along with the associated time). Similarly, as the user completes the lift (e.g., by reaching a certain height or placement of the box 350 on a surface of the shelf 320), the electronic device 360 can record the exact time that the electronic device 360 reached a particular height. Or for example, according to some example embodiments, the accelerometer senses when movement has ended and records the corresponding time stamp associated therewith, for example, in the case where the user completes a lift by placing the box 350 on a surface of the shelf 320.

Thus, according to example embodiments of the present invention, the systems as described herein can preferably be configured in a plurality of different ways so as to obtain data related to the maximal lift capacity of a single manual lift. As described above, the system can comprise one or more repositionable and adjustable sensors such that users of various posture, mechanics, size and flexibility can be assessed accurately and precisely. According to another example embodiment, one or more electronic devices can be incorporated with the system (or at least portions thereof) such that additional data is obtainable. For example, according to some example embodiments, the one or more electronic devices can provide data in real time related to the position thereof in three-dimensional space.

According to one example embodiment, a patient desiring to understand the amount of force being applied to one or more of the feet can stand on the force plates and perform one or more squats or miniature (e.g., shorter) squats. According to some example embodiments, the patient comprises a knee, ankle and/or hip injury or is in need to rehab the same after surgery. According to example embodiments, the patient can stand on the force plates and perform one or more mini squats or other squatting movements. In example embodiments, the electronic device can provide real-time data regarding the forces being applied to the left and right force plates. According to example embodiments, when the patient with the injury is recommended to not apply a specific amount of weight to one or more feet while the particular portion of the body is undergoing rehab, the user can utilize the force plates and see in real time the amount of force being applied thereto so as to obtain a better understanding and mental feeling for the particular force application as prescribed by the therapist.

According to another example embodiment, the systems 10, 300 can provide additional exercises to be captured and output to the electronic devices 200, 400. For example, according to some example embodiments, a carrying test or method is captured by the systems 10, 300 and the data is collected, analyzed, and displayed on the electronic devices 200, 400. According to one example embodiment, the time it takes for a patient to grab or lift the box, walking back a specific distance, and walking back to the initial position where the box was initially positioned is captured. According to example embodiments, the one or more sensors can provide a time stamp with respect to when the box is initially moved or lifted to when the box returns to the desired location. In example embodiments, in the case of the electronic device 360 of the box 350, the entirety of the movement is captured by the electronic device (e.g., as the patient walks to and from the initial position) so as to provide more data relating to the patient's (and box's) total traversed distance, body movement, progress and improvement (e.g., comparing the data of each attempt of one or more exercises).

Optionally, data is obtainable for other exercises, movements, lifts, a carry (or multiple carries) or other interactions with the box and electronic device 360 therein. In example embodiments, the data can be captured, collected and displayed on the electronic device as desired.

Study

In example embodiments, a study was conducted to provide validity to the ability of the functional capacity evaluation system of the present invention to determine maximal lift capacity of a single manual lift. In example embodiments, the aim of the study was to validate the ability of the present invention (e.g., herein referred to as the Polylift™) to determine maximal lift capacity of a single manual lift from waist to shoulder. The Polylift™ is a computerized data collection instrument that is designed to collect information relating to velocity, acceleration, distance, time, and force that can be effectively used in the field of industrial medicine, specifically during Functional Capacity Evaluations. Furthermore, as described above, the Polylift™ comprises a plurality of other unique features, components, etc.

In example embodiments, 41 healthy college students (20—males, 21—females) ages 20 through 27 were voluntarily recruited from Alabama State University College of Health Sciences to participate in the study.

Data collection required two different performance series within a single episode of data collection. First, participants were instructed to perform a repeated lift from waist to shoulder until fatigue, with a standardized load based on each participant's body weight. The number of times each subject correctly performed the lift was entered into Brzycki's 1 Repetition Maximum (1 RM) formula {Load Lifted/1.0278−(reps×0.0278)} for calculation.[2] The second portion of data collection utilized a progressive resistance protocol as the Polylift™ recorded objective measurements of time, acceleration, velocity, and distance during the waist to shoulder lift. The progressive resistance protocol involved one single lift at 25% of 1 RM, 50% of 1 RM, 75% of 1 RM, and 100% of 1 RM.

In example embodiments, a primary finding of this study was that the Polylift™ was able to accurately measure variables of time and acceleration and display a consistent and significant relationship between these variables. As expected, when a person lifts a weight that is closer to their 1 RM, the time required to lift this weight increases, and the acceleration of lifting this weight decreases.

In example embodiments, determining when true maximal lift has been achieved is extremely important during Functional Capacity Evaluations, and practitioners often have difficulty determining when maximal load has been reached based on subjective factors. The Polylift™ was able to objectively recognize maximal lift capacity by accurately demonstrating a consistent, significant decrease in acceleration with increasing loads due to the diminishing ability to generate force.

"The medical and indirect costs of occupational injuries and illnesses are sizable, at least as large as the cost of cancer" (Leigh, 2011). Employers bear the burdens of absenteeism, loss of productivity, increased health care, disability, and workers compensation costs after an employee is injured (Ratzon, Jarus, & Catz, 2007; Schulte, 2005). Often, the employee requires subsequent rehabilitation and may eventually participate in a functional capacity evaluation (Isernhagen, 1992)(Chen, 2007). The United States Department of Labor published that "approximately 2.9 million nonfatal workplace injuries and illnesses [were] reported by private industry employers in 2016" mounting yearly costs of industrial injuries to nearly $192 billion in the year 2007 (*NONFATAL OCCUPATIONAL INJURIES AND ILLNESSES REQUIRING DAYS AWAY FROM WORK,* 2015, 2016) (Leigh, 2011).

With the mentioned statistical data, the effect on the workforce, healthcare and increased occurrence of disability, the role of physical and occupational therapists in the field of industrial medicine has been vital in recent years. Physical therapists, who are noted as movement specialists, are particularly important in industrial medicine due to the fact that "movement is the basis of productive work" (Isernhagen, 1991). Therapists are able to evaluate and treat musculoskeletal disorders, assist in injury prevention, provide ergonomic education, perform functional capacity evaluations, prescribe conditioning exercises, and complete pre-work screening activities (Isernhagen, 1991) Operating in that capacity, therapists first identify and address risk factors along with utilizing gross objective measurements and observation to ascertain an individual's readiness to return to work, their ability to perform optimally on the job and most importantly assist in the prevention of re injury.

A tool that physical therapists utilize within industrial medicine is functional capacity evaluations. These evaluations, as explained by Isernhagen, are effective because they are dynamic, comprehensive and mimic tasks such as lifting, carrying, reaching, squatting and gripping which are vital to effectively perform work (Isernhagen, 1991; Smeets, Hijdra, Kester, Hitters, & Knottnerus, 2006). Functional capacity evaluations are not only functional, as the name suggests, but they relate directly to and are comprised of activities that account for one of the major types of non-fatal injuries that occur which are musculoskeletal disorders. Injuries involving the musculoskeletal system accounted for 31 percent of the total cases reported in 2015 and are typically diagnosed as sprains or strains (*NONFATAL OCCUPATIONAL INJURIES AND ILLNESSES REQUIRING DAYS AWAY FROM WORK,* 2015, 2016) After a diagnosis is made and skilled therapy services are completed, a functional capacity evaluation is often performed utilizing equipment such as handheld dynamometer, Purdue pegboard, weights, step ladder, sled station, weight box and workstation equipped with shelves, heart rate monitor, sphygmomanometer and a stop watch which is assist in collecting measurements. During the evaluation, therapists rely on both subjective information, objective measurements and clinical judgment to assess many of the musculoskeletal aspects of the test (Gross & Battié, 2002).

One of the more popular methods of the evaluation, the kinesiophysical method, involves therapists determining maximal lifting capacity by observing altered lifting mechanics and use of accessory muscles, which does not involve objective measurements or validated equipment (Isernhagen, 1992). While experienced therapists possess clinical judgment and excellent observation skills, a validated machine that can produce data to assist in deciphering if maximal effort has been produced can improve credibility of reports. More importantly functional capacity evaluations that are substantiated with valid equipment can provide tangible evidence to accompany sound clinical judgment and will reinforce evidence provided in medicolegal cases (Gross & Battié, 2002). A machine such as the Polylift™ has the ability to fulfill the above mentioned characteristics and improve both the sensitivity and specificity of a functional capacity evaluation (Gross & Battié, 2002)(Lemstra, Olszynski, & Enright, 2004).

The Polylift™ is a mechanized data collection machine that is constructed to mimic a lifting workstation. The machine consists of a force plate, a box for weights and adjustable shelves equipped with arm portions and sensors to detect motion within the sagittal plane (see FIG. 1). The machine is accompanied by a computer which collects information such as time, velocity, acceleration, and distance of the weight box during the functional lifts (typically performed in an evaluation) from floor to waist, waist to shoulder and shoulder to overhead. To collect data, the clinician first uses the computerized software to identify which type of lift will be performed. Once the subject lifts the box, the lower laser beam is triggered to start collecting data. When the higher laser beam is triggered, the data collection ends for that lift. Information regarding amount of time required to complete the lift, the velocity and the acceleration of the attempt is recorded by the computerized software. The force plate also records the weight of the subject and provides data on the amount of foot pressure being placed through both feet throughout the lift.

The goal of this study was to validate the results of the data collected by the Polylift™. In order to do so, researchers had to prove that as the weight lifted by the participants increased, the acceleration of the lift decreased and the amount of time increased.

To validate the Polylift™, repeated repetitions at a submaximal level were utilized to ascertain the amount of repetitions that could be completed with a target of below ten repetitions. With that information, the Brzycki's One Repetition Maximum (1 RM) formula (Amarante, Cyrino, & Nakamura, 2007) was used to determine the maximal lifting capacity and assess if the machine is able to detect changes in acceleration and time with increasing loads. The Polylift™ would then be validated if it accurately, and significantly produced data that agreed with Newton's second law of motion (F=mass×acceleration) indicated by a decrease in acceleration and increase in time with increasing load.

The subject sample was one of convenience drawn from the College of Health Sciences at Alabama State University. 41 college students (20—Male, 21—Female), ages between 20 to 27 volunteered to participate in this study. The exclusion criteria were: any "yes" response noted on the Physical Activity Readiness Questionnaire (PAR-Q), the presence of back pain within the last year, or history of cardiac issues. Exclusion criteria was selected specifically to ensure the safety of the participants (Adams, 1999). After clarity of the study's purpose and procedures were established, all participants signed an informed consent form. Also, all subjects were free to withdraw from the study or stop testing at any time. Participation length requirement was a single day of data collection. Variables compared were age, weight, sex, and race. A baseline heart rate measurement was utilized to maintain an objective measurement for the subject's safety, as well as serve as a baseline for continuing the second half of data collection.

One Repetition Maximum (1 RM) Determination: A standardized lift from waist to shoulder was chosen to be performed for this study (Abdul-Hameed, Rangra, Shareef, & Hussain, 2012). Waist to shoulder lifting is a commonly utilized technique in many Functional Capacity Evaluations. Safe lifting guidelines provided by the *Occupational Safety and Health Administration Technical Manual*[7] were utilized as protocol along with correct demonstration from an investigator ("OSHA Technical Manual (OTM)|Occupational Safety and Health Administration," 2014). Each subject's one repetition maximum prediction was calculated by using the submaximal repeated lift equation developed by Brzycki (Amarante et al., 2007)(Mayhew, Johnson, Lamonte, Lauber, & Kemmler, 2008). Each subject's starting lift load was chosen by using a standardized maximum lift chart based on the subject's body weight (Kisner, Colby, & Borstad, 2018). All subjects were blind to the amount of weight placed inside the box. The starting waist position height was set at 35" from the floor, and the shoulder height at 55" from the floor (Savage, Jaffrey, Billing, & Ham, 2015) (Blache, Desmoulins, Allard, Plamondon, & Begon, 2015). The subjects were instructed to perform the repeated lift as many times as possible with the same technique and form until fatigue (Smith, 1994)(Gardener & McKenna, 1999).

Prior to the investigation, operational definitions established by Gross et al. were observed by researchers in order to determine when maximal effort has been exceeded and when to safely stop the lift (Gross & Battik 2002). After completion of the repeated lift, the number of times each subject correctly performed the lift was inserted into Brzycki's 1 RM formula {Load Lifted/1.0278−(reps× 0.0278)} for calculation (Amarante et al., 2007). Subjects were then required to take 15 minute rest break or to reach at least 80% of resting heart rate before proceeding with the Polylift™ data collection portion.

Polylift™ Data Collection: The second portion of data collection utilized a progressive resistance protocol and the Polylift's™ ability to record the objective measurements time, acceleration, velocity, and distance. The progressive resistance protocol involved one lift of each of the following loads: 25% of 1 RM, 50% of 1 RM, 75% of 1 RM, and 100% of 1RM. The subjects were completely blind to their established 1 RM and the amount of load used for each single trial. The Polylift's™ specialized data collection system was utilized while the subject maintained safe form and technique established with each lift. In between each trial, the subjects were allotted at least a 1 minute rest break, as established by Matuszak et al. as sufficient time for recovery during 1 RM testing (Matuszak, Fry, Weiss, Ireland, & McKnight, 2003).

Results

The criteria adopted to determine the 1 RM produced results of subjects lifting between 12 and 65 pounds for 1-18 repetitions. Those results assisted in determining the computation of the subject's 1 RM using the Brzycki formula. The resistance progression is demonstrated in Table 1 below.

TABLE 1

Descriptive Statistics of Load lifted by Test Subjects (n = 41)

| Variables | Range | Mean | Standard Deviation |
|---|---|---|---|
| Initial Load lifted | 12-65. lbs | 38.262 | 15.800 |
| Repetitions | 1-38 repetitions | 7.929 | 4.319 |
| 25% of 1 RM | 3.86-26.07 lbs. | 12.394 | 6.095 |
| 50% of 1 RM | 4-52.14 lbs. | 24.700 | 12.331 |
| 75% of 1 RM | 11.57-78.21 lbs. | 37.182 | 18.285 |
| 100% of 1 RM | 15.43-104.29 lbs. | 49.577 | 24.382 |

In table 1, the data demonstrates the variable load lifted between subjects ranging from 12-65 pounds in the initial calculation of 1 rep max using the Brzycki formula and 15.43-104.29 pounds during the actual 1 RM lift.

TABLE 2

Mean time & Acceleration during trials of progressive resistance.

| Variable | Mean Time (Seconds) | Standard deviation for time (seconds) | Mean acceleration (m/s) | Standard deviation for acceleration (m/s) |
|---|---|---|---|---|
| 15% of 1 RM | 0.342 seconds | 0.117 seconds | 245.104 m/s$^2$ | 196.385 m/s$^2$ |
| 50% of 1 RM | 0.354 seconds | 0.086 seconds | 185.567 m/s$^2$ | 79.557 m/s$^2$ |
| 75% of 1 RM | 0.416 seconds | 0.100 seconds | 132.909 m/s$^2$ | 52.687 m/s$^2$ |
| 100% of 1 RM | 0.548 seconds | 0.204 seconds | 85.607 m/s$^2$ | 41.080 m/s$^2$ |

In table 2, the data demonstrates the mean time and acceleration change with each stage of progression. The results of this study demonstrate how the mean time consistently increases with each stage of progression from 0.342 to 0.548 seconds. Therefore the Polylift™ recognizes that as the weight gets heavier, the test subject requires more time to successfully lift the weight. The results also demonstrate a rapid decrease in acceleration with each stage of progression.

In example embodiments, the data demonstrates at 25% of a test subject's 1 RM, time and acceleration were significantly ($p<0.05$) correlated ($r=-0.795$, $p<001$). This indicates that as acceleration decreases, time increases. At 100% of a test subject's 1 RM, time and acceleration were significantly ($p<0.05$) correlated ($r=-0.835$, $p<0.001$). This indicates that as acceleration decreases, time increases.

In example embodiments, a repeated measures ANOVA was conducted to analyze the time needed to lift 25%, 50%, 75%, and 100% of a test subject's 1 RM. There was a statistically significant effect on time across the four conditions, $F(3, 123)=40.874$, $p<0.001$) with significant level set at $p<0.05$. Post hoc analysis pairwise comparisons utilizing LSD method further revealed that there were significant differences ($p<0.01$) in time between all conditions except for between 25% of 1 RM and 50% of 1 RM ($p=0.347$).

In example embodiments, the pattern of the results suggests that as the weight lifted by the participants increased, the acceleration of the lift decreased and the amount of time increased. The variables of time and acceleration were both consistently and significantly (p<0.05) correlated with time increasing as acceleration decreased at both 25% of 1 RM and 100% of 1 RM. There were significant differences in the amount of time for a participant to lift 25%, 50%, 75%, and 100% of their 1 RM. In comparing each of these four conditions, there was a significant increase in time required to lift the weight in all conditions except for 25% and 50% of the 1 RM. There were significant differences in the acceleration required to lift 25%, 50%, 75%, and 100% of the participant's 1 RM. In comparing each of these four conditions, there was a significant decrease in acceleration between all four conditions. A primary finding of this study is that the Polylift™ machine is able to accurately measure variables of time and acceleration and display a consistent and significant relationship between these variables. As expected, when a person lifts a weight that is closer to their 1 RM, the time required to lift this weight increases, and the acceleration of lifting this weight decreases.

In example embodiments, the study utilized established theories and validated calculations to assist in the validation of the machine. Newton's second law of motion, which involves the variables of mass and acceleration during the production of force, was the basis of the hypothesized outcome. The formula Force=Mass×Acceleration establishes an inverse relationship between the variables thus an increase in the force required to move an object of a higher weight would result in a decrease in acceleration. Because lifting involves an object being moved through space with either submaximal or maximal force, the time to move the heavier object from one point to the other should increase as the load increases. Advantageously, all of the mentioned variables involved in the task of lifting are able to be collected by the Polylift™, as demonstrated in this study.

Another calculation involved in the study was the validated Brzycki formula which is a commonly used tool to assess muscle strength. In order to generate force, strength is a vital factor to successfully perform a lift and cause change in acceleration. The formula provided the 1 RM for each subject and was used to progress the resistance. The Polylift™ demonstrated the ability to detect changes in the variables. In reviewing the results, it was significantly demonstrated that the Polylift™ is able to indicate maximal lift capacity by accurately demonstrating a consistent decrease in acceleration with increasing loads due to the diminishing ability to generate force. In particular, the load lifted at 25% of 1 RM and 100% of 1 RM demonstrated the Polylift's™ ability to detect a considerable difference in acceleration between both lifts. Moreover, there was a correlation coefficient between the load lifted and the change in acceleration demonstrated by the Polylift™ as the resistance increased.

It should be mentioned that there were some results during the 25% of 1 RM lift that were not expected. When reviewed, these results produced slower acceleration rates when compared to the acceleration of the 50% 1 RM lift. Researchers hypothesize that this can be attributed to the subject being cautious with the first trial after the completing submaximal lifts of a moderate weight in the initial data collection portion of the study. This occurrence brings to the forefront the many complex factors involved, especially the psychological aspect of lifting (Kaplan, Wurtele, & Gillis, 1996). The use of established theories assisted greatly in the testing and subsequent results of significant findings. The data from this study suggests that the use of the Polylift™ to determine maximal lifting capacity will deliver valid results indicated by the change in variables during the lifting procedure.

Conclusion

The significance of the results in this study demonstrate that the Polylift™ is able to indicate maximal lift capacity by accurately demonstrating a consistent decrease in acceleration with increasing loads due to the diminishing ability to generate force. Physical therapists who are well versed in ergonomics and the area of human performance now have available to them a validated piece of equipment that provides objective measurements to assist in determining an individual's readiness to return to work. The use of the Polylift™ during functional capacity evaluations and rehabilitation in general allows therapist not to rely solely on their observational skills or subjective reports from the patient but reveal through change in time and acceleration if physical "effort" matches the expected outcomes.

While the invention has been described with reference to preferred and example embodiments, it will be understood by those skilled in the art that a variety of modifications, additions and deletions are within the scope of the invention, as defined by the following claims.

What is claimed is:

1. A functional capacity evaluation system comprising:
a rack comprising a standing platform, at least one repositionable shelf, at least one arm portion movably mounted to the rack, and at least one sensor mounted to at least a portion of the arm portion,
wherein the at least one arm portion is configured to be adjustably secured thereto an expanded configuration and a retracted configuration and a substantially horizontal orientation and a substantially vertical orientation, wherein the adjustability of the at least one arm portion is configured to be independent relative to the repositionability of the at least one shelf.

2. The functional capacity evaluation system of claim 1, further comprising at least one force sensor provided with the standing platform so as to measure one or more separate loads applied thereto.

3. The functional capacity evaluation system of claim 1, wherein the arm portion generally extends outwardly from the rack or shelf nearby, and wherein the arm portion comprises a fastener so as to provide adjustability to the same between the substantially horizontal orientation and the substantially vertical orientation.

4. The functional capacity evaluation system of claim 1, wherein the at least one arm portion is movably mounted to the rack and configured to both traverse between an expanded configuration and a retracted configuration and pivot between a substantially horizontal orientation and a substantially vertical orientation.

5. The functional capacity evaluation system of claim 1, wherein at least two arm portions are movably mounted on opposite sides of the at least one shelf, wherein the arm portions are adjustable between an expanded configuration and a retracted configuration.

6. The functional capacity evaluation system of claim 5, wherein the arm portions are further adjustable between a substantially horizontal orientation and a substantially vertical orientation.

7. The functional capacity evaluation system of claim 1, further comprising a control system connected to the at least one sensor and an electronic device, wherein data output from the at least one sensor is received by the control system, and wherein the control system outputs the data to the electronic device.

8. The functional capacity evaluation system of claim 7, wherein the electronic device receives the data from the control system and outputs the same to a visual screen thereof, the data corresponding to at least one parameter selected from the group consisting of the weight of a lifting box, the distance of the lift, the time or duration of the lift, average velocity, average acceleration, average force, the average loads of each foot of the user during the lift, or the foot disparity between the average loads of each foot.

9. A functional capacity evaluation system comprising:
a rack comprising at least one shelf and a standing platform generally positioned on a ground surface near the rack;
a lifting box, the lifting box comprising at least one grasping handle and a retaining area such that one or more weights or weighted objects can be contained therein:
at least one sensor mounted to at least a portion of the rack;
a control module connected to the at least one sensor;
first electronic device connected with the control module, the first electronic device comprising an application such that data from the at least one sensor can be collected, processed, calculated and displayed on the first electronic device; and
a second electronic device coupled with at least a portion of the lifting box, the second electronic device configured to communicate with the control module, the electronic device and/or the database,
wherein the at least one sensor that is mounted to at least a portion of the rack comprises a 3D capture sensor, the 3D capture sensor being in communication with the second electronic device such that the position of the second electronic device and lifting box thereof relative to the position of the 3D capture sensor, in three-dimensional space, can be captured in real time.

10. The functional capacity evaluation system of claim 9, further comprising a server or database for collecting and storing data obtained from the at least one sensor, control module and/or electronic devices, wherein the control module and/or electronic devices are connected to a network, and wherein the database is connected to the network so as to provide a channel of communication between the server and the control module and/or electronic devices such that data can be sent and received therebetween.

11. The functional capacity evaluation system of claim 9, wherein the second electronic device is configured to obtain data in real time related to the movement, position, orientation, velocity and/or acceleration of the same and lifting box thereof when a user lifts the lifting box.

12. The functional capacity evaluation system of claim 9, wherein the second electronic device can obtain its position in three-dimensional space relative to the 3D capture sensor.

13. The functional capacity evaluation system of claim 9, further comprising at least one load cell or sensor connected to the standing platform.

14. A method of using a functional capacity evaluation system comprising:
providing a functional capacity evaluation rack comprising a standing area or platform, one or more height-adjustable shelves, and at least one arm support member, the arm support member comprising a sensor mounted thereto;
providing a lifting box to be lifted by a user;
adjusting the at least one arm support member and sensor mounted thereto so that a user lifting the lifting box from a ground surface to a desired height does not unintentionally trigger the sensor during lifting, the at least one arm support member and sensor mounted thereto being adjustable between a generally horizontal orientation and a generally vertical orientation, the adjustability of the at least one arm portion being independent of the height adjustability of the one or more shelves; and
performing at least one lift, wherein a user lifts the lifting box from the standing area to a desired height, wherein the sensor captures the user's lift movement so as to provide data related to the time at which the user both begins and completes the lift.

15. The method of claim 14, further comprising providing a control module for collecting the data from the at least one sensor.

16. The method of claim 14, further comprising providing an electronic device for collecting the data from the at least one sensor.

* * * * *

UNITED STATES PATENT AND TRADEMARK OFFICE
CERTIFICATE OF CORRECTION

| | |
|---|---|
| PATENT NO. | : 11,383,131 B2 |
| APPLICATION NO. | : 16/600199 |
| DATED | : July 12, 2022 |
| INVENTOR(S) | : Bridges et al. |

It is certified that error appears in the above-identified patent and that said Letters Patent is hereby corrected as shown below:

In the Claims

In Claim 1, Column 20, Line 31:
'adjustably secured thereto an expanded configuration'
Should read as follows:
'adjustably secured thereto between an expanded configuration'

Signed and Sealed this
Fourth Day of October, 2022

Katherine Kelly Vidal
*Director of the United States Patent and Trademark Office*